United States Patent [19]

Kawakita et al.

[11] Patent Number: 5,185,333
[45] Date of Patent: Feb. 9, 1993

[54] BENZAZINE COMPOUNDS AND PHARMACEUTICAL USES THEREOF

[75] Inventors: Takeshi Kawakita; Takanobu Kuroita, both of Oita; Takemi Fukuda, Hyogo; Ryuhei Iezawa, Oita, all of Japan

[73] Assignee: Yoshitomi Pharmaceutical Industries, Ltd., Osaka, Japan

[21] Appl. No.: 721,011

[22] Filed: Jun. 26, 1991

Related U.S. Application Data

[63] Continuation-in-part of Ser. No. 547,551, Jul. 3, 1990, abandoned.

[30] Foreign Application Priority Data

Jul. 3, 1989 [JP] Japan .................................. 1-171549
Mar. 12, 1990 [JP] Japan .................................. 2-60663

[51] Int. Cl.$^5$ .................. A61K 31/54; A61K 31/535; C07D 279/16; C07D 265/36
[52] U.S. Cl. .................. 514/224.2; 514/230.5; 544/52; 544/105; 544/73
[58] Field of Search .................. 544/73, 52, 105, 58.1, 544/58.6; 514/230.5, 224.2

[56] References Cited

U.S. PATENT DOCUMENTS

| | | | |
|---|---|---|---|
| 4,778,792 | 10/1988 | Lesieur et al. | 514/230.5 |
| 4,826,839 | 5/1989 | King et al. | 514/214 |
| 4,892,872 | 1/1990 | Tahara et al. | 514/230.5 |
| 4,933,445 | 6/1990 | Pelletier et al. | 540/552 |
| 4,935,511 | 6/1990 | Youssefyeh et al. | 540/552 |
| 4,937,337 | 6/1990 | Leinert et al. | 514/211 |

FOREIGN PATENT DOCUMENTS

| | | |
|---|---|---|
| 0234872 | 9/1987 | European Pat. Off. |
| 0313393 | 4/1989 | European Pat. Off. |
| 2509155 | 9/1976 | Fed. Rep. of Germany |

*Primary Examiner*—Nicholas S. Rizzo
*Assistant Examiner*—Matthew V. Grumbling
*Attorney, Agent, or Firm*—Sughrue, Mion, Zinn, Macpeak & Seas

[57] ABSTRACT

A benzazine compound, a geometrical isomer of said benzazine compound, an optical isomer of said benzazine compound, and a pharmaceutically acceptable salt of said benzazine compound, said benzazine compound being represented by formula (I):

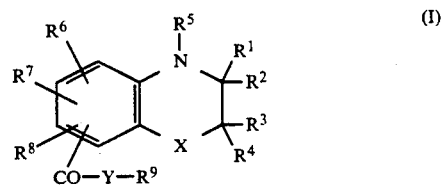

wherein each symbol is as defined in the specification. Said benzazine compounds exhibit 5-HT$_3$ receptor antagonistic activity, and 5-HT$_{1A}$ receptor and/or 5-HT$_2$ receptor and/or dopamine D$_2$ receptor blocking activity so that they are useful as drugs for the prophylaxis or treatment of various digestive diseases vomiting and disturbances in central nervous systems and the like. The intermediates for said benzazine compounds are also disclosed.

11 Claims, No Drawings

BENZAZINE COMPOUNDS AND PHARMACEUTICAL USES THEREOF

This is a continuation-in-part application of Ser. No. 07/547,551 filed on Jul. 3, 1990, now abandoned.

BACKGROUND OF THE INVENTION

It has been ascertained that 5-HT$_3$ receptors, which are of one class of the subtypes of the serotonin (5-HT) receptors, are not only present in the sensory nervous system and the autonomic nervous system, but distributed in the central nervous system. As the whole aspect of the 5-HT$_3$ receptors is being revealed, it has been suggested that the clinical application of antagonistic drugs for the receptors can range widely from the peripheries to the center.

It has been known that the compounds showing an antagonistic activity for 5-HT$_3$ receptors are useful for the treatment of disturbances in central nervous systems such as depression, anxiety, schizophrenia and dementia, for the prophylaxis or treatment of digestive diseases such as indigestion, nausea, vomiting, diarrhea, indefinite complaint of alimentary system, irritable bowel syndrome, and/or for the relief or treatment of dependance induced by drug abuse. As such 5-HT$_3$ receptor-blocking agent, ICS 205-930 ((3α-tropanyl)-1H-indole-3-carboxylic acid ester), Ondansetron (1,2,3,9-tetrahydro-9-methyl-3[(2-methyl-1H-imidazole-1-yl)methyl]-4H-carbazole-4-one) and the like are known. Further, U.S. Pat. No. 4,892,872 discloses 3-oxo-2H-1,4-benzoxazine-8-carboxamide compounds which shows an antagonistic activity for 5-HT$_3$ receptors. Further, a certain class of benzamides have a dopamine D$_2$ receptor-blocking activity and are useful as drugs for the treatment of schizophrenia or as anti-vomiting drugs. For example, Sulpiride (2-methoxy-N-(1-ethyl-2-pyrrolidinylmethyl)-5-sulfamoylbenzamide) is being used as a drug for the treatment of schizophrenia or peptic ulcer, while Metoclopramide (4-amino-5-chloro-N-(2-diethylamine)ethyl-2-methoxybenzamide) is being used as prokinetics or as anti-vomiting drugs.

As a result of studies made by the present inventors, a series of novel compounds having a different structure from those of the above-mentioned compounds and having a 5-HT$_3$ receptor-blocking activity and/or a 5-HT$_{1A}$ receptor-blocking activity and/or a 5-HT$_2$ receptor-blocking activity and/or dopamine D$_2$ receptor-blocking activity were found.

SUMMARY OF THE INVENTION

The present invention provides a benzazine compound, its geometrical isomer and optical isomer, and a pharmaceutically acceptable salt thereof, all of which are novel compounds that are pharmacologically active and useful as medicines and an intermediate thereof and a pharmaceutical use of said benzazine compound.

DETAILED DESCRIPTION OF THE INVENTION

The present invention provides a benzazine compound, a geometrical isomer of said benzazine compound, an optical isomer of said benzazine compound, and a pharmaceutically acceptable salt of said benzazine compound, said benzazine compound being represented by formula (I):

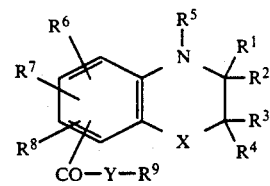
(I)

wherein both $R^1$ and $R^2$ represent hydrogen; $R^3$ and $R^4$ are the same or different and each represents hydrogen, an alkyl, phenyl or a phenylalkyl, provided that one of $R^3$ and $R^4$ represents hydrogen, an alkyl, phenyl or a phenylalkyl and the another represents an alkyl, phenyl or a phenylalkyl when $R^9$ represents a group of formula (a) or (c) as defined below; $R^5$ represents hydrogen, an alkyl, or a phenylalkyl; $R^6$ represents hydrogen, a halogen, an alkoxy, amino, nitro, —S(O)$_l R^{18}$ (wherein $R^{18}$ represents an alkyl, phenyl or a substituted phenyl and $l$ is 0, 1 or 2), or

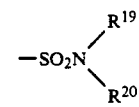

(wherein $R^{19}$ and $R^{20}$ are the same or different and each represents hydrogen or an alkyl); both $R^7$ and $R^8$ represent hydrogen; X represents oxygen or sulfur; Y represents —NH—; and $R^9$ represents a group of the formula:

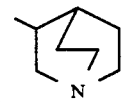
(a)

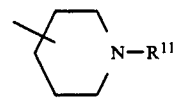
(b)

wherein $R^{11}$ represents an alkyl, a phenylalkyl, or a substituted phenylalkyl,

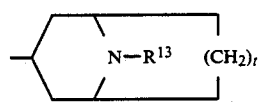
(c)

wherein $t$ is 0 or 1 and $R^{13}$ represents an alkyl, a phenylalkyl, or a substituted phenylalkyl,

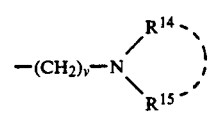
(d)

wherein $R^{14}$ and $R^{15}$ are bonded to each other to be a group which forms a heterocyclic ring in cooperation with the adjacent nitrogen atom, and $v$ is an integer of 1 to 8, or

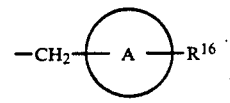
(f)

wherein ring A represents 2-pyrrolidine or 2-morpholine, and $R^{16}$ represents hydrogen, an alkyl, an alkenyl, an alkynyl, a phenylalkyl, a substituted phenylalkyl, amino, a mono- or dialkyl-substituted amino, or an acylamino.

The present invention further provides a compound or a reactive derivative on a carboxyl group thereof, said compound being represented by formula (II):

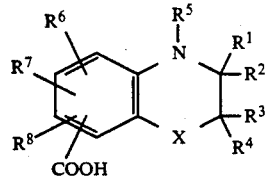
(II)

wherein each symbol has the same meaning as that defined above.

The present invention still provides a pharmaceutical composition comprising the benzazine compound of formula (I) above, an isomer thereof or a pharmaceutically acceptable salt thereof.

The above definition is explained below in more detail. The halogen can be fluorine, chlorine, bromine, or iodine; the alkyl can be one having 1 to 20 carbon atoms, such as methyl, ethyl, propyl, isopropyl, butyl, isobutyl, tertiary butyl, pentyl, hexyl, heptyl, octyl, nonyl, decyl, dodecyl, tetradecyl, octadecyl, icosyl, or the like; the alkoxy can be one having 1 to 8 carbon atoms, such as methoxy, ethoxy, propoxy, isopropoxy, butoxy, isobutoxy, tertiary butoxy, pentyloxy, hexyloxy, heptyloxy, octyloxy, or the like; the phenylalkyl can be benzyl, 1- or 2-phenylethyl, 3-phenylpropyl, 4-phenylbutyl, or the like. The group which forms a heterocyclic ring in cooperation with the adjacent nitrogen atom can be a cyclic amino group which may contain, besides the nitrogen atom, a hetero atom such as nitrogen, oxygen, sulfur, etc., and examples of such group include 5- to 7-membered saturated cyclic amino groups such as pyrrolidinyl, morpholino, thiomorpholino, piperidino, piperazinyl, homopiperazinyl, and the like. This cyclic amino group may contain a substituent group at a position where substitution is possible, and examples of such substituent group include an alkyl, phenyl, a substituted phenyl, a phenylalkyl, a substituted phenylalkyl, an alkanoyl, and the like. The substituent group(s) contained in the substituted phenyl, substituted phenylalkyl and substituted phenoxyalkyl can be 1 to 3 substituents selected from halogens, alkoxys, alkyls, nitro, amino, haloalkyl (the haloalkyl can be one having 1 to 4 carbon atoms, such as trifluoromethyl, 2,2,2-trifluoroethyl, 2,3,3-trifluoropropyl, 1,1,2,2-tetrafluoroethyl, 2,2,3,3-tetrafluoropropyl, or the like), carboxy, and alkoxycarbonyls (these halogens, alkyls and alkoxys are the same as defined above).

Among the compounds of the present invention, compounds of formula (I) wherein $R^9$ represents a group of formula (a) or (c) are preferred as one embodiment of the present invention. Also, compounds of formula (I) wherein $R^9$ represents a group of formula (b), (d) or (f) are preferred as another embodiment of the present invention.

Among these compounds, 6-chloro-2,2,4-trimethyl-N-(3-quinuclidinyl)-3,4-dihydro-2H-1,4-benzoxazine-8-carboxamide, (R)-6-chloro-2,2,4-trimethyl-N-(3-quinuclidinyl)-3,4-dihydro-2H-1,4-benzoxazine-8-carboxamide, (S)-6-chloro-2,2,4-trimethyl-N-(3-quinuclidinyl)-3,4-dihydro-2H-1,4-benzoxazine-8-carboxamide, endo-6-chloro-2,2,4-trimethyl-N-(9-methyl-9-azabicyclo[3.3.1]non-3-yl)-3,4-dihydro-2H-1,4-benzoxazine-8-carboxamide, N-[(1-butyl-2-pyrrolidinyl)methyl]-4-methyl-6- methylthio-3,4-dihydro-2H-1,4-benzoxazine-8-carboxamide, (S)-(−)-N-[(1-butyl-2-pyrrolidinyl)methyl]-6-chloro-4-methyl-3,4-dihydro-2H-1,4-benzoxazine-8-carboxamide, 6-amino-N-[(1-butyl-2-pyrrolidinyl)methyl]-4-methyl-3,4-dihydro-2H-1,4-benzoxazine-8-carboxamide, 6-chloro-4-methyl-N-[(1-butyl-2pyrrolidinyl)methyl]-3,4-dihydro-2H-1,4-benzoxazine-8-carboxamide, (R)-(+)-6-chloro-4-methyl-N-[(1-nonyl-2-pyrrolidinyl)methyl]-3,4-dihydro-2H-1,4-benzoxazine-8-carboxamide, 6-chloro-4-methyl-N-[(1-ethyl-2-pyrrolidinyl)methyl]-3,4-dihydro-2H-1,4-benzoxazine-8-carboxamide, (S)-N-[(1-butyl-2-pyrrolidinyl)methyl]-4-methyl-6-methylthio-3,4-dihydro-2H-1,4-benzoxazine-8-carboxamide, (R)-N-[(1-butyl-2-pyrrolidinyl)methyl]-4-methyl-6-methylthio-3,4-dihydro-2H-1,4-benzoxazine-8-carboxamide, (S)-N-[{1-(2-phenylethyl)-2-pyrrolidinyl}methyl]-4-methyl-6-nitro-3,4-dihydro-2H-1,4-benzoxazine-8-carboxamide, (R)-N-[{1-(2-phenylethyl)-2-pyrrolidinyl} methyl]-4-methyl-6-nitro-3,4-dihydro-2H-1,4-benzoxazine-8-carboxamide, (S)-N-[{1-(2-phenylethyl)-2-pyrrolidinyl}methyl]-6-amino-4-methyl-3,4-dihydro-2H-1,4-benzoxazine-8-carboxamide, and (R)-N-[(1-benzyl-2-pyrrolidinyl)methyl]-4-methyl-6-methylthio-3,4-dihydro-2H-1,4-benzoxazine-8-carboxamide, and pharmaceutically acceptable salts thereof are preferred.

The compounds of formula (I) according to the present invention can be prepared by the following methods.

Compounds of general formula (I) can be produced by reacting a carboxylic acid represented by formula (II) as mentioned above or a reactive derivative thereof with a compound represented by formula (III)

$R^9$—YH     (III)

(wherein each symbol has the same meaning as that defined above).

(a) In the case where the compound of formula (II) is a free carboxylic acid, the reaction is carried out in an inert solvent, with cooling or heating or at room temperature, in the presence of a condensing agent such as dicyclohexylcarbodiimide, titanium tetrachloride, a phosphorus halide (phosphorus trichloride, phosphorus oxychloride, etc.), diethyl chlorophosphite, o-phenylene chlorophosphite, ethyl dichlorophosphite, or the like. Compound (III) may be treated beforehand with a phosphorus halide in an inert solvent before it is subjected to condensation with compound (II). For example, in the case where the phosphorus halide is phosphorus trichloride, compound (III) is treated beforehand, with cooling or at room temperature, with about ½ mol of phosphorus trichloride in an inert solvent in the presence of a tertiary base such as triethylamine, pyridine, N,N-dimethylaniline, or the like, and the resulting compound (III) is then reacted with compound (II) in an inert solvent at room temperature or with heating, preferably with heat refluxing.

(b) In the case where a reactive derivative of the carboxylic acid of formula (II) is employed and the derivative is an acid halide such as acid chloride or acid bromide, the reaction is carried out in an inert solvent, with cooling or at room temperature, in the presence of a tertiary base such as triethylamine, pyridine, N,N-dimethylaniline, or the like, or the reaction is carried out in water, with cooling or at room temperature, in the presence of an alkali such as sodium hydroxide, potassium hydroxide, or the like.

(c) In the case where as a reactive derivative of compound (II), use is made of a symmetric acid anhydride or a mixed anhydride such as an alkylcarbonic mixed anhydride, an alkylphosphate mixed anhydride, an alkylphosphite mixed anhydride, an alkylsulfuric mixed anhydride, or the like, the reaction is carried out in an inert solvent, with cooling or heating or at room temperature, in the presence of a tertiary base such as triethylamine, pyridine, N,N-dimethylaniline, N-methylmorpholine, or the like.

(d) In the case where as a reactive derivative of compound (II), an active amide such as an acid imidazolide, an acid pyrrolidide, 2,4-dimethylpyrazolide, or the like is used, the reaction is conducted in an inert solvent at room temperature or with heating.

(e) The compound according to the present invention may also be reacted with that reactive derivative of compound (II) which is an ester such as a methyl ester, an ethyl ester, a p-nitrophenyl ester, a p-chlorophenyl ester, or the like. This reaction is effected in an inert solvent (the compound (III) may be used in excess so as to serve also as a solvent) at room temperature or with heating, preferably with heat refluxing.

The inert solvent used in each of the above-described condensation reactions can be benzene, toluene, xylene, methanol, ethanol, isopropyl alcohol, diethyl ether, dioxane, tetrahydrofuran, chloroform, dichloromethane, dichloroethane, hexamethylphosphoric triamide, diethylene glycol, dimethylformamide, ethyl acetate, or the like, or a mixture of these solvents. In the case where a reactive derivative of compound (II) is used, a proper solvent is selected according to the kind of the derivative.

The compound of general formula (II) can, for example, be produced by the following reaction routes.

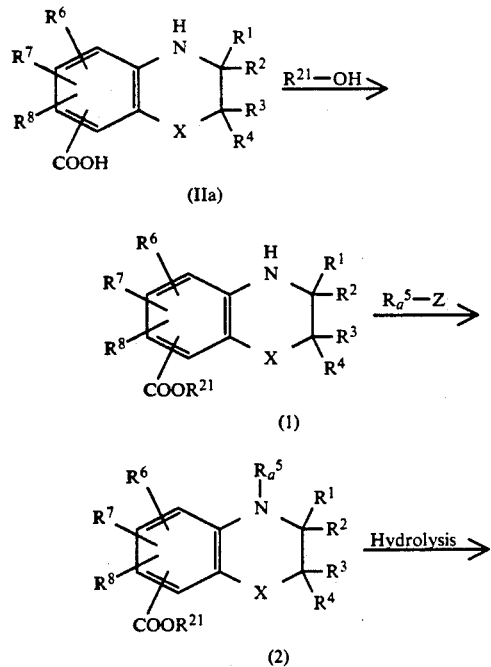

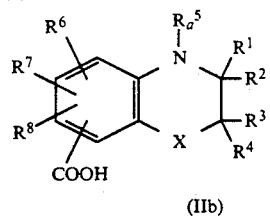

(In the above route, $R_a^5$ represents the same group as $R^5$ excluding hydrogen, $R^{21}$ represents an ester residue, Z represents a group to be eliminated which may be chlorine, bromine, iodine, methanesulfonyloxy, p-toluenesulfonyloxy, or the like, and the other symbols have the same meanings as those defined above.)

Compound (IIa) for use in the above process can be obtained according to the method proposed by G. Coudert et al. (*Synthesis*, p.541, 1979). Compound (IIb) can be prepared by reacting compound (1), which is obtained by the esterification of compound (IIa), with $R_a^5$-Z in the presence of a tertiary base such as, for example, triethylamine or an inorganic salt such as, for example, potassium carbonate, and hydrolyzing the thus-obtained compound (2) with an alkali.

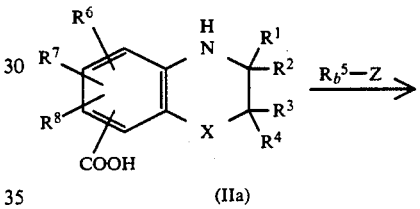

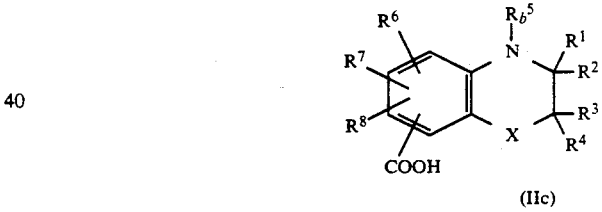

(In the above route, $R_b^5$ represents an alkanoyl, an aroyl, or a heteroaroyl and the other symbols have the same meanings as those defined above.)

Compound (IIc) can be produced by reacting compound (IIa) with $R_b^5$-Z in the presence of a tertiary base such as, for example, triethylamine or an inorganic salt such as, for example, potassium carbonate.

Of the compounds of the present invention which are represented by formula (I) wherein $R^3$ and $R^4$ are different, those containing a chiral carbon are obtained in the form of a racemic mixture. The optical isomers in each of such racemic mixtures are within the scope of the present invention. If desired, such a racemic mixture can be optically resolved by an ordinary method that employs an optically active acid (tartaric acid, dibenzoyltartaric acid, mandelic acid, 10-camphorsulfonic acid, or the like) to utilize the basicity of the racemic mixture. Further, an intended compound (I) having a desired configuration can be stereo selectively produced by subjecting to the abovedescribed condensation reaction an optically active carboxylic acid obtained by optical resolution of the racemate (II) by use of an optically active base (cinchonine, cinchonidine, brucine, quinine, α-methylbenzylamine, or the like) or a reactive derivative of the optically active carboxylic acid together with an optically active compound (III) separately prepared by resolving with an optically active acid (tartaric acid, dibenzoyltartaric acid, mandelic acid, 10-camphorsulfonic acid, or the like).

Geometrical isomers also can be prepared according to ordinary methods.

The compound of general formula (I) can be converted into a pharmaceutically acceptable acid-adduct salt, such as hydrochloride, hydrobromide, phosphate, sulfate, p-toluenesulfonate, citrate, lactate, maleate, fumarate, tartrate, or the like.

The following experiments will illustrate potent pharmacological activities of the compounds (I) of the present invention.

PHARMACOLOGICAL EXPERIMENT 1

Antagonistic Effect Against Von Bezold-Jarish Reflex

5-HT$_3$ receptor blocking effects of the test compounds of the present invention and the compounds for comparison were evaluated based on the antagonistic effects against von Bezold-Jarish reflex caused by administering serotonin to anesthetized rats as an index according to Forzard's method described in *Naunyu-schmiedeberq's Arch. Pharmacol.*, vol.326, pp36, 1984.

Male Wistar rats weighing 350–450 g were anesthetized with an intraperitoneal injection of 1.25 g/kg of urethane. The left jugular vein was cannulated for the intravenous injection and the left femoral vein was cannulated for the measurement of blood pressure and heart rate. Serotonin (20 µg/kg) was intravenously injected, and the test compound was intravenously injected 5 minutes before the challenge with serotonin. The antagonistic activity of the test compounds against the caused reflex bradycardia was measured and the effective dose (ED$_{50}$, µg/kg), the dose required to antagonize the maximum activity by 50%, was determined. The results are summarized in Table 1.

TABLE 1

| Test Compound | ED$_{50}$ (µg/kg. i.v.) |
|---|---|
| Compound for comparison A | 0.28 |
| Compound for comparison B | 0.73 |
| Compound for comparison C | 0.096 |
| Compound of Example 1 | 0.12 |
| Compound of Example 2 | 0.17 |
| Compound of Example 3 | 0.11 |
| Compound of Example 26 | 0.24 |

Notes;
Compound for comparison A: 6-chloro-4-methyl-N-(3-quinuclidinyl)-3,4-dihydro-2H-1,4-benzoxazine-8-carboxamide hydrochloride
Compound for comparison B: (R)-6-chloro-4-methyl-N-(3-quinuclidinyl)-3,4-dihydro-2H-1,4-benzoxazine-8-carboxamide
Compound for comparison C: (S)-6-chloro-4-methyl-N-(3-quinuclidinyl)-3,4-dihydro-2H-1,4-benzoxazine-8-carboxamide Notes;
Compound for comparison A: 6-chloro-4-methyl-N-(3-quinuclidinyl)-3,4-dihydro-2H-1,4-benzoxazine-8-carboxamide hydrochloride
Compound for comparison B: (R)-6-chloro-4-methyl-N-(3-quinuclidinyl)-3,4-dihydro-2H-1,4-benzoxazine-8-carboxamide
Compound for comparison C: (S)-6-chloro-4-methyl-N-(3-quinuclidinyl)-3,4-dihydro-2H-1,4-benzoxazine-8-carboxamide Next, the test compound (the compounds of Examples 3 and 26 and Compound for comparison C) was intravenously injected 15, 30, 45, 60 or 120 minutes before the intravenous injection of serotonin and the antagonistic activity against von Bezold-Jarish reflex of the test compound was measured in the similar manner as described above, and the effective dose (ED$_{50}$, µg/kg) was determined. The results are summarized in Table 2.

| Test Compound | ED$_{50}$ (µg/kg. i.v.) | | | | | |
|---|---|---|---|---|---|---|
| | 5* | 15* | 30* | 45* | 60* | 120* |
| Compound of Example 3 | 0.11 | 0.09 | 0.08 | 0.11 | 0.11 | 0.32 |
| Compound of Example 26 | 0.24 | 0.15 | 0.11 | 0.10 | 0.11 | 0.12 |
| Compound for comparison C | 0.096 | 0.16 | 0.43 | 0.46 | 1.09 | 2.12 |

Note*:
The interval (minutes) between the injection of the test compound and the injection of serotonin

PHARMACOLOGICAL EXPERIMENT 2

Dopamine D$_2$ Binding Test

Specific dopamine D$_2$ receptor binding test was conducted in accordance with the method described in *European Journal of Pharmacology*, vol.46, page 377, 1977.

Crude synaptosome fraction was separated from corpus striatum of 9 to 10 weeks-aged Wistar rats and suspended into 50 mM tris-hydrochloric acid buffer solution (pH 7.1) containing 120 mM sodium chloride, 5 mM potassium chloride, 2 mM calcium chloride, 1 mM magnesium chloride, 10 µM pargyline and 0.1% ascorbic acid.

Next, to the resulting synaptosome suspension were added the test compound of the present invention at several concentrations and tritium Spiperone at the terminal concentration of 0.2 nM, and the mixture was allowed to react at 37° C. for 20 minutes. After completion of the reaction, the reaction mixture was suction filtered through Whatman GF/B glass filter. The glass filter was washed with 50 mM tris-hydrochloric acid buffer solution (pH 7.7), and then the radioactivity of the residue remaining on the glass filter was measured by liquid scintillation counter. Non-specific binding was determined under the presence of 100 µM of (±)-Sulpiride. 50% Inhibition concentration (IC$_{50}$) of the test compound was graphically determined and the inhibition constant (Ki value) was calculated. The results are summarized in Table 3.

PHARMACOLOGICAL EXPERIMENT 3

Serotonin 1A (5-HT$_{1A}$) Binding Test

Specific serotonin 1A (5-HT$_{1A}$) receptor binding test was conducted in accordance with the manner described in *Journal of the Neurochemistry*, vol.44, page 1685, 1985.

Crude synaptosome fraction was separated from hippocampus of 9 to 10 weeks-aged Wistar rat and suspended into 50 mM tris-hydrochloric acid buffer solution (pH 7.4) containing 1 mM manganese chloride.

Next, to the resulting synaptosome suspension were added the test compound of the present invention at several concentrations and tritium 8-OH-DPAT at the terminal concentration of 0.2 nM, and the mixture was allowed to react at 37° C. for 12 minutes. After completion of the reaction, the reaction mixture was suction filtered through Whatman GF/B glass filter. The glass filter was washed with 50 mM tris-hydrochloric acid buffer solution (pH 7.4), and then the radioactivity of the residue remaining on the glass filter was measured by liquid scintillation counter. Non-specific binding was determined under the presence of $10^{-5}$M of serotonin (5-HT). 50% Inhibition concentration (IC$_{50}$) of test compound was graphically determined and the inhibition constant (Ki value) was calculated. The results are summarized in Table 3.

PHARMACEUTICAL EXPERIMENT 4

Serotonin 2 (5-HT$_2$) Binding Test ($^3$H-Ketanserin Binding Test)

Preparation of crude synaptosome fraction and binding assay were conducted according to the method reported in Molecular Pharmacology, vol. 21, page 301, 1981 by Leysen et al.

Freezed cerebral cortex dissected out from rats were homogenized in 30 fold-volumes of ice-cold 0.32 M sucrose solution and the suspension was centrifuged at 1000×g for 10 minutes at 0° C. The supernatant was centrifuged at 40,000×g for 20 minutes at 0° C. and the resulting pellet was homogenized in 30 fold-volumes of ice-cold 50 mM Tris-HCl buffer (pH 7.7), and incubated at 37° C. for 10 minutes. The suspension was centrifuged at 40,000×g for 20 minutes at 0° C. again. The resulting pellet was homogenized in 100 fold-volumes of the above buffer and provided as synaptosome membranes solution for the next assay.

To the aliquots (900 μl) of synaptosome membranes solution were added 50 μl of $^3$H-Ketanserin solution at the terminal concentration of 0.2 nM and 50 μl of test compound solution or 50 μl of its medium, and incubated at 37° C. for 20 minutes. After completion of the reaction, the mixture was rapidly vacuum-filtered through Whatman GF/B filters. The filters were washed three times with 5 ml of the above buffer, and then the radioactivity of the residue remaining on the filters was measured by liquid scintillation counter. Nonspecific binding was determined under the presence of 10 μM of mianserin. 50% Inhibition concentration (IC$_{50}$) of the test compound was graphically determined and the inhibition constant (Ki value) was calculated. The results are summarized in Table 3.

TABLE 3

| Test Compound (Example No.) | Dopamine D$_2$ binding test Ki(M) | 5-HT$_{1A}$ binding test Ki(M) | 5-HT$_2$ binding test Ki(M) |
|---|---|---|---|
| 7 | $2.5 \times 10^{-8}$ | $7.5 \times 10^{-7}$ | — |
| 8 | $1.5 \times 10^{-8}$ | $6.2 \times 10^{-8}$ | $4.0 \times 10^{-8}$ |
| 13 | $6.9 \times 10^{-7}$ | $2.4 \times 10^{-6}$ | — |
| 18 | $6.1 \times 10^{-9}$ | $1.4 \times 10^{-8}$ | $1.5 \times 10^{-8}$ |
| 19 | $6.3 \times 10^{-7}$ | $4.2 \times 10^{-7}$ | $1.4 \times 10^{-7}$ |
| 21 | $1.2 \times 10^{-8}$ | $3.4 \times 10^{-8}$ | $1.5 \times 10^{-8}$ |
| 39 | $3.6 \times 10^{-9}$ | $1.9 \times 10^{-8}$ | — |
| 40 | $1.7 \times 10^{-8}$ | $1.2 \times 10^{-7}$ | $2.2 \times 10^{-8}$ |
| 42 | $2.1 \times 10^{-7}$ | $7.5 \times 10^{-9}$ | — |
| 43 | $5.2 \times 10^{-8}$ | $5.1 \times 10^{-8}$ | — |
| 44 | $4.2 \times 10^{-9}$ | $1.7 \times 10^{-8}$ | $2.7 \times 10^{-8}$ |
| 56 | — | $1.8 \times 10^{-8}$ | — |

All ddy male mice survived by the oral administration (100 mg/kg) and the intraperitoneal injection (50 mg/kg) of the test compounds of the present invention for 5 days.

As apparent from the results of various pharmacological experimentations including the experiments above, the compounds of the present invention show a highly potent and long-lasting 5-HT$_3$ receptor antagonistic activity and possess affinities with 5-HT$_{1A}$ and/or 5-HT$_2$ and/or dopamine D$_2$ receptors, and are hence, useful for the prophylaxis or treatment of digestive diseases such as indigestion, delayed gastric emptying, diarrhea, indefinite complaint of alimentary system, irritable bowel syndrome, peptic ulcer and/or the treatment for migraine headache, cluster headache, arrhythmia, or nausea and vomiting, especially, nausea and vomiting induced by the administration of carcinostatic substances, nausea and vomiting induced by radiotherapy, disturbances in central nervous systems such as dementia, depression, anxiety, schizophrenia, drug abuse and material dependence, or the treatment for dystrophy or sentimental affection such as excitement or aggression accompanied by dyskinesia, senescence, cerebrovascular disease, or alcohol dependence.

In order that the compounds of the present invention be used as drugs and safely administered to patients, a therapeutically effective amount of the compounds are normally admixed with pharmaceutically acceptable carriers, excipients, diluents, and other ingredients and formulated into tablets (including sugar-coated tablets and film-coated tablets), granules, powders, injections, etc. The dosage may vary depending on the condition, body weight, age, etc. of the patient, but it may generally be about 0.1 to 100 mg/kg per day for an adult in the case of oral administration. The daily administration is preferably effected at a time or effected in several doses.

FORMULATION EXAMPLE 1

| Compound obtained in Example 1 | 10.0 mg |
|---|---|
| Lactose | 30.0 mg |
| Corn starch | 19.8 mg |
| Crystalline cellulose | 28.0 mg |
| Talc | 2.0 mg |
| Magnesium stearate | 0.2 mg |
| Total | 90.0 mg |

The compound obtained in Example 1, lactose, corn starch, and crystalline cellulose were mixed and kneaded, with a part of the corn starch being used as a binder paste, and the resulting blend was granulated and then dried at 50° C. for 3 hours.

The dry granules were passed through a 24-mesh sieve, and then talc and magnesium stearate were added to the granules. The resulting mixture was formed into tablets each weighing 90 mg, by means of a rotary pelletizing machine of the punching type employing a pounder having a diameter of 6.0 mm. Subsequently, a film coating containing hydroxypropyl methyl cellulose and titanium oxide as base materials was formed over each of the above-obtained tablets in an amount of 5 mg per tablet.

FORMULATION EXAMPLE 2

| Compound obtained in Example 1 | 5.0 mg |
|---|---|
| Sodium chloride | 18.0 mg |
| Distilled water for injection in total | 2.0 ml |

Sodium chloride was dissolved in about 80 parts of water for use in injection, and the compound obtained in Example 1 was then added thereto and dissolved. Subsequently, the volume of the solution was adjusted to the total volume (100 parts). The resulting solution was filtered through a membrane filter (0.2 μm), charged into a 2-ml ampoule, and then sterilized at 115° C. for 30 minutes, thereby producing an injection.

The present invention will be explained below in detail by means of the following Reference Examples and Examples, but the present invention should not be limited to these Examples.

REFERENCE EXAMPLE 1

A mixture of 12 g of 6-chloro-3,4-dihydro-2H-1,4-benzoxazine-8-carboxylic acid, 200 ml of methanol, and 10 ml of concentrated sulfuric acid was heat-refluxed for 24 hours with stirring. The liquid reaction mixture was concentrated in vacuo. To the residue were added an aqueous solution of sodium hydrogencarbonate and ethyl acetate, and the resulting organic layer was separated, washed with water, and dried over magnesium sulfate. The solvent was clitilled off under reduced pressure, and the residue was recrystallized from a mixed solvent of isopropyl ether and ethanol to give 9.2 g of methyl 6-chloro-3,4-dihydro-2H-1,4-benzoxazine-8-carboxylate. Melting point: 60°-61° C.

REFERENCE EXAMPLE 2

To a solution of 9.2 g of methyl 6-chloro-3,4-dihydro-2H-1,4-benzoxazine-8-carboxylate and 6.7 g of potassium carbonate in 100 ml of dimethylformamide was added 6.4 g of methyl iodide with cooling and stirring. The resulting mixture was heated at 70° C. for 2 hours with stirring. The liquid reaction mixture was added to 200 ml of water, and the resulting insoluble substance was filtered off, washed with water, and dried, thereby obtaining 7.1 g of methyl 6-chloro-4-methyl-3,4-dihydro-2H-1,4-benzoxazine-8-carboxylate. Melting point: 91°-92° C.

REFERENCE EXAMPLE 3

7.1 Grams of methyl 6-chloro-4-methyl-3,4-dihydro-2H-1,4-benzoxazine-8-carboxylate and 3.8 g of sodium hydroxide were dissolved in a mixed solvent obtained by mixing 50 ml of methanol and 100 ml of water, and the resulting solution was heated at 70° C. for 2 hours with stirring. The liquid reaction mixture was added to 300 ml of water, and 6 ml of concentrated hydrochloric acid was added thereto. The resulting insoluble substance was filtered off, washed with water, and dried, thereby obtaining 5.8 g of 6-chloro-4-methyl- 3,4-dihydro-2H-1,4-benzoxazine-8-carboxylic acid. Melting point: 202°-204° C.

REFERENCE EXAMPLE 4

A solution of 10 g of 6-chloro-3,4-dihydro-2H-1,4-benzoxazine-8-carboxylic acid and 6.5 ml of triethylamine in 100 ml of chloroform was cooled, and 4.4 g of acetyl chloride was added thereto with stirring. The resulting mixture was stirred at room temperature for 2 hours. To the liquid reaction mixture were added an aqueous solution of sodium hydrogen carbonate and chloroform, and the resulting organic layer was separated, washed with water, and then dried with magnesium sulfate. The solvent was distilled off under reduced pressure, thereby obtaining 7.8 g of 4-acetyl-6-chloro-3,4-dihydro-2H-1,4-benzoxazine-8-carboxylic acid. Melting point: 76°-77° C.

According to methods similar to Reference Examples above, following compounds were produced.

6-Chloro-4-ethyl-3,4-dihydro-2H-1,4-benzoxazine-8-carboxylic acid. Melting point: 76°-77° C.

4-Butyl-6-chloro-3,4-dihydro-2H-1,4-benzoxazine-8-carboxylic acid. Melting point: 116°-118° C.

6-Chloro-4-(2-phenylethyl)-3,4-dihydro-2H-1,4-benzoxazine-8-carboxylic acid. Melting point: 128°-129° C.

6-Chloro-4-(2-chlorobenzyl)-3,4-dihydro-2H-1,4-benzoxazine-8-carboxylic acid. Melting point: 308° C. (decomposed).

6-Chloro-4-(3-chlorobenzyl)-3,4-dihydro-2H-1,4-benzoxazine-8-carboxylic acid. Melting point: 292° C. (decomposed).

6-Chloro-4-(4-chlorobenzyl)-3,4-dihydro-2H-1,4-benzoxazine-8-carboxylic acid. Melting point: 163°-164° C.

4-Benzoyl-6-chloro-3,4-dihydro-2H-1,4-benzoxazine-8-carboxylic acid. Melting point: 175°-176° C.

6-Chloro-4-(4-fluorobenzyl)-3,4-dihydro-2H-1,4-benzoxazine-8-carboxylic acid. Melting point: 133°-135° C.

6-Fluoro-4-methyl-3,4-dihydro-2H-1,4-benzoxazine-8-carboxylic acid. Melting point: 164°-166° C.

6-Bromo-4-methyl-3,4-dihydro-2H-1,4-benzoxazine-8-carboxylic acid. Melting point: 192°-194° C.

4-Acetyl-3,4-dihydro-2H-1,4-benzoxazine-8-carboxylic acid. Melting point: 143° C.

4-Acetyl-6-nitro-3,4-dihydro-2H-1,4-benzoxazine-8-carboxylic acid. Melting point 243° C. (decomposed).

4-Methyl-3,4-dihydro-2H-1,4-benzoxazine-8-carboxylic acid. Melting point: 117° C.

4-Methyl-6-nitro-3,4-dihydro-2H-1,4-benzoxazine-8-carboxylic acid. Melting point: 235° C. (decomposed).

4-Methyl-6-sulfamoyl-3,4-dihydro-2H-1,4-benzoxazine-8-carboxylic acid. Melting point: 234° C. (decomposed).

4-Methyl-6-methylthio-3,4-dihydro-2H-1,4-benzoxazine-8-carboxylic acid. Melting point: 170°-172° C.

6-Methylsulfonyl-4-methyl-3,4-dihydro-2H-1,4-benzoxazine-8-carboxylic acid. Melting point: 215°-217° C.

6-Chloro-2,2,4-trimethyl-3,4-dihydro-2H-1,4-benzoxazine-8-carboxylic acid. Melting point: 172°-174° C.

6-Chloro-2,2-diphenyl-4-methyl-3,4-dihydro-2H-1,4-benzoxazine-8-carboxylic acid. Melting point: 176°-178° C.

2,2,4-Trimethyl-3,4-dihydro-2H-1,4-benzoxazine-8-carboxylic acid. Melting point: 125°-127° C.

6-Chloro-2,2-dimethyl-4-ethyl-3,4-dihydro-2H-1,4-benzoxazine-8-carboxylic acid. Melting point: 159°-160° C.

6-Chloro-2,2-dimethyl-4-propyl-3,4-dihydro-2H-1,4-benzoxazine-8-carboxylic acid. Melting point: 139°-141° C.

6-Fluoro-2,2,4-trimethyl-3,4-dihydro-2H-1,4-benzoxazine-8-carboxylic acid. Melting point: 148°-150° C.

6-Bromo-2,2,4-trimethyl-3,4-dihydro-2H-1,4-benzoxazine-8-caroxylic acid. Melting point: 155°-157° C.

2,2,4-Trimethyl-3,4-dihydro-2H-1,4-benzoxazine-8-carboxylic acid. Melting point: 125°-127° C.

4-Butyl-6-chloro-2,2-dimethyl-3,4-dihydro-2H-1,4-benzoxazine-8-carboxylic acid. Melting point: 104°-106° C.

4-Benzyl-6-chloro-2,2-dimethyl-3,4-dihydro-2H-1,4-benzoxazine-8-carboxylic acid. Melting point: 130°-131° C.

6-Chloro-2,2-dimethyl-4-(2-pheylethyl)-3,4-dihydro-2H-1,4-benzoxazine-8-carboxylic acid. Melting point: 96°-97° C.

6-Chloro-2,4-dimethyl-3,4-dihydro-2H-1,4-benzoxazine-8-carboxylic acid. Melting point: 158°-159° C.

6-Chloro-2-methyl-4-phenyl-3,4-dihydro-2H-1,4-benzoxazine-8-carboxylic acid. Melting point: 165°-166° C.

6-Chloro-4-methyl-3,4-dihydro-2H-1,4-benzothiazine-8-carboxylic acid. Melting point: 243°-245° C.

EXAMPLE 1

1.53 Grams of 6-chloro-2,2,4-trimethyl-3,4-dihydro-2H-1,4-benzoxazine-8-carboxylic acid was dissolved in 30 ml of ethyl acetate, and 0.848 g of triethylamine was added thereto. While the resulting mixture was being cooled with ice at −10° to −5° C., 0.794 g of pivaloyl chloride was added dropwise. After this mixture was stirred at that temperature for 15 minutes, 0.906 g of 3-aminoquinuclidine was added at a temperature of −10° to −5° C., and the resulting mixture was stirred at room temperature for 1 hour. The liquid reaction mixture was washed with water, dried with anhydrous magnesium sulfate, and then condensed. Ethanolic hydrochloric acid was added to the residue, and the crystals precipitated were filtered off and then recrystallized from ethanol, thereby obtaining 6-chloro-2,2,4-trimethyl-N-(3-quinuclidinyl)-3,4-dihydro-2H-1,4-benzoxazine-8-carboxamide hydrochloride as colorless crystals. Melting point: 266° C. (decomposed).

EXAMPLE 2

1.53 Grams of 6-chloro-2,2,4-trimethyl-3,4-dihydro-2H-1,4-benzoxazine-8-carboxylic acid was dissolved in 30 ml of ethyl acetate, and 0.848 g of triethylamine was added thereto. While the resulting mixture was being cooled with ice at −10° to −5° C., 0.794 g of pivaloyl chloride was added dropwise. After this mixture was stirred at that temperature for 15 minutes, 0.906 g of (R)-3-aminoquinuclidine was added at a temperature of −10° to −5° C., and the resulting mixture was stirred at room temperature for 1 hour. The liquid reaction mixture was washed with water, dried with anhydrous magnesium sulfate, and then condensed. Ethanolic hydrochloric acid was added to the residue, and the crystals precipitated were filtered off and then recrystallized from ethanol, thereby obtaining (R)-6-chloro-2,2,4-trimethyl-N-(3-quinuclidinyl)-3,4-dihydro-2H-1,4-benzoxazine-8-carboxamide hydrochloride as colorless crystals. Melting point: 272° C. (decomposed). $[\alpha]_D = -3.6°$ (c=0.5, H$_2$O).

EXAMPLE 3

1.53 Grams of 6-chloro-2,2,4-trimethyl-3,4-dihydro-2H-1,4-benzoxazine-8-carboxylic acid was dissolved in 30 ml of ethyl acetate, and 0.848 g of triethylamine was added thereto. While the resulting mixture was being cooled with ice at −10° to −5° C., 0.794 g of pivaloyl chloride was added dropwise. After this mixture was stirred at that temperature for 15 minutes, 0.906 g of (S)-3-aminoquinuclidine was added at a temperature of −10° to −5° C., and the resulting mixture was stirred at room temperature for 1 hour. The liquid reaction mixture was washed with water, dried with anhydrous magnesium sulfate, and then condensed. Ethanolic hydrochloric acid was added to the residue, and the crystals precipitated were filtered off and then recrystallized from ethanol, thereby obtaining (S)-6-chloro-2,2,4-trimethyl-N-(3-quinuclidinyl)-3,4-dihydro-2H-1,4-benzoxazine-8-carboxamide hydrochloride as colorless crystals. Melting point: 273° C. (decomposed). $[\alpha]_D = +3.4°$ (c=0.5, H$_2$O).

EXAMPLE 4

A solution of 3.5 g of 6-chloro-4-methyl-3,4-dihydro-2H-1,4-benzoxazine-8-carboxylic acid and 3.3 g of N-methylmorpholine in 100 ml of tetrahydrofuran was cooled to 5° C. or below, and 2.3 g of isobutyl chlorocarbonate was added thereto with stirring. Stirring was then continued for 30 minutes. To the liquid reaction mixture was added 3 g of 4-amino-1-benzylpiperidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with an ethanol solution of fumaric acid to convert the residue into a fumarate form. This fumarate was recrystallized from ethanol, thereby obtaining 6-chloro-4-methyl-N-(1-benzyl-4-piperidyl)-3,4-dihydro-2H-1,4-benzoxazine-8-carboxamide fumarate. Melting point: 232°-233° C.

EXAMPLE 5

A solution of 2.3 g of 6-chloro-4-methyl-3,4-dihydro-2H-1,4-benzoxazine-8-carboxylic acid and 2.8 g of triethylamine in 30 ml of ethyl acetate was cooled to 5° C. or below, and 1.3 g of pivaloyl chloride was added thereto with stirring. Stirring was then continued for 30 minutes. To the liquid reaction mixture was added 2.1 g of 3-amino-1-benzylpiperidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was recrystallized from isopropyl alcohol, thereby obtaining 6-chloro-4-methyl-N-(1-benzyl-3-piperidyl)-3,4-dihydro-2H-1,4-benzoxazine-8-carboxamide. Melting point: 109°-110° C.

EXAMPLE 6

A solution of 1.30 g of 6-chloro-4-methyl-3,4-dihydro-2H-1,4-benzoxazine-8-carboxylic acid and 1.15 g of triethylamine in 20 ml of ethyl acetate was cooled to 5° C. or below, and 0.79 g of pivaloyl chloride was added thereto with stirring. Stirring was then continued for 30 minutes. To the liquid reaction mixture was added 0.80 g of 8-methyl-8-azabicyclo[3.2.1]octan-3-amine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was recrystallized from isopropyl alcohol, thereby obtaining 6-chloro-4-methyl-N-(8-methyl-8-azabicyclo[3.2.1]oct-3-yl)-3,4-dihydro-2H-1,4-benzoxazine-8-carboxamide. Melting point: 183°-185° C.

EXAMPLE 7

A solution of 4.5 g of 6-chloro-4-methyl-3,4-dihydro-2H-1,4-benzoxazine-8-carboxylic acid and 4.0 g of triethylamine in 60 ml of ethyl acetate was cooled to 5° C. or below, and 2.7 g of pivaloyl chloride was added thereto with stirring. Stirring was then continued for 30 minutes. To the liquid reaction mixture was added 2.5 g of 2-aminomethyl-1-ethylpyrrolidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with ethanolic hydrochloric acid to convert the residue into a hydrochloride form. This hydrochloride was recrystallized from ethanol, thereby obtaining 6-chloro-4-methyl-N-[(1-ethyl-2-pyrrolidinyl)methyl]-3,4-dihydro-2H-1,4-benzoxazine-8-carboxamide hydrochloride. Melting point: 197° C. (decomposed).

EXAMPLE 8

A solution of 4.5 g of 6-chloro-4-methyl-3,4-dihydro2H-1,4-benzoxazine-8-carboxylic acid and 4.0 g of triethylamine in 60 ml of ethyl acetate was cooled to 5° C. or below, and 2.7 g of pivaloyl chloride was added thereto with stirring. Stirring was then continued for 30 minutes. To the liquid reaction mixture was added 3.1 g of 2-aminomethyl-1-butylpyrrolidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with ethanolic hydrochloric acid to convert the residue into a hydrochloride form. This hydrochloride was recrystallized from ethanol, thereby obtaining 6-chloro-4-methyl-N-[(1-butyl-2-pyrrolidinyl)methyl]-3,4-dihydro-2H-1,4-benzoxazine-8-carboxamide hydrochloride. Melting point: 158°-159° C.

EXAMPLE 9

A solution of 1.5 g of 6-chloro-4-methyl-3,4-dihydro-2H-1,4-benzoxazine-8-carboxylic acid and 1.34 g of triethylamine in 40 ml of ethyl acetate was cooled to 5° C. or below, and 0.79 g of pivaloyl chloride was added thereto with stirring. Stirring was then continued for 30 minutes. To the liquid reaction mixture was added 0.86 g of 1-(2-aminoethyl)morpholine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with an ethanol-hydrochloric acid to convert the residue into a hydrochloride form. This hydrochloride was recrystallized from ethanol, thereby obtaining 6-chloro-4-methyl-N-(2-morpholinoethyl)-3,4-dihydro-2H-1,4-benzoxazine-8-carboxamide hydrochloride. Melting point: 190°-191° C.

EXAMPLE 10

A solution of 1.5 g of 6-chloro-4-methyl-3,4-dihydro-2H-1,4-benzoxazine-8-carboxylic acid and 1.34 g of triethylamine in 40 ml of ethyl acetate was cooled to 5° C. or below, and 0.79 g of pivaloyl chloride was added thereto with stirring. Stirring was then continued for 30 minutes. To the liquid reaction mixture was added 0.85 g of 1-(2-aminoethyl)piperidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with an ethanol-hydrochloric acid to convert the residue into a hydrochloride form. This hydrochloride was recrystallized from ethanol, thereby obtaining 6-chloro-4-methyl-N-(2-piperidinoethyl)-3,4-dihydro-2H-1,4-benzoxazine-8-carboxamide hydrochloride. Melting point: 137°-139° C.

EXAMPLE 11

A solution of 1.5 g of 6-chloro-4-methyl-3,4-dihydro-2H-1,4-benzoxazine-8-carboxylic acid and 1.34 g of triethylamine in 40 ml of ethyl acetate was cooled to 5° C. or below, and 0.79 g of pivaloyl chloride was added thereto with stirring. Stirring was then continued for 30 minutes. To the liquid reaction mixture was added 0.77 g of 1-(2-aminoethyl)pyrrolidine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, thereby obtaining 6-chloro-4-methyl-N-[2-(1-pyrrolidinyl)ethyl]-3,4-dihydro-2H-1,4-benzoxazine-8-carboxamide. Melting point: 88°-89° C.

EXAMPLE 12

A solution of 1.5 g of 6-chloro-4-methyl-3,4-dihydro-2H-1,4-benzoxazine-8-carboxylic acid and 1.34 g of triethylamine in 40 ml of ethyl acetate was cooled to 5° C. or below, and 0.79 g of pivaloyl chloride was added thereto with stirring. Stirring was then continued for 30 minutes. To the liquid reaction mixture was added 0.91 g of 3-aminomethyl-1-benzylmorpholine, and the resulting mixture was stirred at room temperature for 2 hours. To this mixture were then added an aqueous solution of sodium hydrogen carbonate and ethyl acetate, and the resulting organic layer was separated, washed with water, and dried with magnesium sulfate. The solvent was distilled off under reduced pressure, and the residue was treated with an ethanol-hydrochloric acid to convert the residue into a hydrochloride form. This hydrochloride was recrystallized from ethanol, thereby obtaining 6-chloro-4-methyl-N-[(1-benzyl-3-morpholinyl)methyl]-3,4-dihydro-2H-1,4-benzoxazine-8-carboxamide hydrochloride. Melting point: 154°-156° C.

EXAMPLE 13

A solution of 2.0 g of 6-chloro-4-methyl-3,4-dihydro-2H-1,4-benzoxazine-8-carboxylic acid and 1.1 g of N-methylmorpholine in 10 ml of dimethylformamide and 20 ml of tetrahydrofuran was cooled to −15° to −20° C., and 1.2 g of a isobutyl chloroformate was added thereto with stirring. Stirring was then continued for 25 minutes. To the liquid reaction mixture was added 2.0 g of (R)-(+)-2-aminomethyl-1-nonylpyrrolidine, and the resulting mixture was stirred at room temperature for 2 hours. The resulting mixture was concentrated under reduced pressure to obtain a residue. To the residue were then added an aqueous solution of sodium hydrogen carbonate and ethyl acetate, and the resulting organic layer was separated, washed with water, and dried with magnesium sulfate. The solvent was distilled off under reduced pressure, and the residue was separated and purified by means of a silica gel column chromatography, thereby obtaining (R)-(+)-6-chloro-4-methyl-N-[(1-nonyl-2-pyrrolidinyl)methyl]-3,4-dihydro-2H-1,4-benzoxazine-8-carboxamide as oil. [α]_D= +58.3° (c=1, methanol).

EXAMPLE 14

A solution of 2.28 g of 6-chloro-4-methyl-3,4-dihydro-2H-1,4-benzoxazine-8-carboxylic acid and 3 ml of triethylamine in 10 ml of dimethylformamide and 50 ml of tetrahydrofuran was cooled to −15° to −20° C., and 1.45 ml of isobutyl chloroformate was added thereto with stirring. Stirring was then continued for 20 minutes. To the liquid reaction mixture was added 1.7 g of (R)-(+)-2-aminomethyl-1-butylpyrrolidine, and the resulting mixture was stirred at room temperature for 4 hours. The reaction mixture was concentrated under reduced pressure to obtain a residue. To the residue were then added an aqueous solution of sodium hydrogen carbonate and ethyl acetate, and the resulting organic layer was separated, washed with water, and dried with magnesium sulfate. The solvent was distilled off under reduced pressure, and the residue was separated and purified by means of silica gel column chromatography, thereby obtaining (R)-(+)-N-[(1-butyl-2-pyrrolidinyl)methyl]-6-chloro-4-methyl-3,4-dihydro-2H-1,4-benzoxazine-8-carboxamide as oil. [α]_D= −62.7° (c=1, methanol)

EXAMPLE 15

A solution of 6.0 g of 4-methyl-6-nitro-3,4-dihydro-2H-1,4-benzoxazine-8-carboxylic acid and 5 g of N-methylmorpholine in 30 ml of dimethylformamide and 20 ml of ( tetrahydrofuran was cooled to −15° to −20° C., and 3.4 g of isobutyl chloroformate was added thereto with stirring. Stirring was then continued for 25 minutes. To the liquid reaction mixture was added 3.9 g of 2-aminomethyl-1-butylpyrrolidine, and the resulting mixture was stirred at room temperature for 4 hours. The reaction mixture was concentrated under reduced pressure to obtain a residue. To the residue were then added an aqueous solution of potassium carbonate and ethyl acetate, and the resulting organic layer was separated, washed with water, and dried with magnesium sulfate. The solvent was distilled off under reduced pressure, and the residue was recrystallized from isopropyl ether, thereby obtaining N-[(1-butyl-2-pyrrolidinyl)methyl]-4-methyl-6-nitro-3,4-dihydro-2H-1,4-benzoxazine-8-carboxamide. Melting point: 88°–89° C.

EXAMPLE 16

A solution of 3 g of 4-methyl-3,4-dihydro-2H-1,4-benzoxazine-8-carboxylic acid and 2.4 g of N-methylmorpholine in 7 ml of dimethylformamide and 15 ml of tetrahydrofuran was cooled to −15° to −20° C., and 2.1 g of isobutyl chloroformate was added thereto with stirring. Stirring was then continued for 20 minutes. To the liquid reaction mixture was added 2.4 g of 2-aminomethyl-1-butylpyrrolidine, and the resulting mixture was stirred at room temperature for 4 hours. The reaction mixture was concentrated under reduced pressure to obtain a residue. To the residue were then added an aqueous solution of potassium carbonate and ethyl acetate, and the resulting organic layer was separated, washed with water, and dried with magnesium sulfate. The solvent was distilled off under reduced pressure, thereby obtaining N-[(1-butyl-2-pyrrolidinyl)methyl]-4-methyl-3,4-dihydro-2H-1,4-benzoxazine-8-carboxamide.

NMR spectra (CDCl_3; ppm): δ=0.9 (t, 3H), 2.9 (s, 3H), 3.3 (t, 2H), 4.38 (t, 2H), 6.6–7.6 (m, 3H), 7.9–8.3 (br, 1H)

EXAMPLE 17

A solution of 2 g of 4-methyl-6-sulfamoyl-3,4-dihydro-2H-1,4-benzoxazine-8-carboxylic acid and 1.1 g of N-methylmorpholine in 30 ml of dimethylformamide and 10 ml of tetrahydrofuran was cooled to −15° to −20° C., and 1 g of isobutyl chloroformate was added thereto with stirring. Stirring was then continued for 20 minutes. To the liquid reaction mixture was added 1.15 g of 2-aminomethyl-1-butylpyrrolidine, and the resulting mixture was stirred at room temperature for 4 hours. The reaction mixture was concentrated under reduced pressure to obtain a residue. To the residue were then added an aqueous solution of potassium carbonate and ethyl acetate, and the resulting organic layer was separated, washed with water, and dried with magnesium sulfate. The solvent was distilled off under reduced pressure, and the residue was recrystallized from isopropyl ether, thereby obtaining N-[(1-butyl-2-pyrrolidinyl)methyl]4-methyl-6-sulfamoyl-3,4-dihydro-2H-1,4-benzoxazine-8-carboxamide. Melting point: 144°–145° C.

EXAMPLE 18

A solution of 0.8 g of 4-methyl-6-methylthio-3,4-dihydro-2H-1,4-benzoxazine-8-carboxylic acid and 0.5 g of N-methylmorpholine in 5 ml of dimethylformamide and 5 ml of tetrahydrofuran was cooled to −15° to −20° C., and 0.45 g of isobutyl chloroformate was added thereto with stirring. Stirring was then continued for 20 minutes. To the liquid reaction mixture was added 0.52 g of 2-aminomethyl-1-butylpyrrolidine, and the resulting mixture was stirred at room temperature for 4 hours. To this mixture were then added an aqueous solution of potassium carbonate and ethyl acetate, and the resulting organic layer was separated, washed with water, and dried with magnesium sulfate. The solvent was distilled off under reduced pressure, thereby obtaining N-[(1-butyl-2-pyrrolidinyl)methyl]-4-methyl-6-methylthio-3,4-dihydro-2H-1,4-benzoxazine-8-carboxamide.

NMR spectra (CDCl_3; ppm): δ=0.9 (t, 3H), 2.46 (s, 3H), 2.9 (s, 3H), 3.3 (t, 2H), 4.36 (t, 2H), 6.67 (d, 1H), 7.42 (d, 1H), 7.9–8.3 (br, 1H)

EXAMPLE 19

To a solution of 2 g of N-[(1-butyl-2-pyrrolidinyl)methyl]-4-methyl-6-nitro-3,4-dihydro-2H-1,4-benzoxazine-8-carboxamide in 150 ml of methanol was added 0.7 g of palladium-on-carbon to conduct reduction reaction under atmospheric pressure with charging hydrogen gas. The catalyst was filtered out, and the solvent was distilled off under reduced pressure. The residue was treated with an ethanol solution of fumaric acid to convert the residue into fumarate form. This fumarate was recrystallized from ethanol, thereby obtaining 6-amino-N-[(1-butyl-2-pyrrolidinyl)methyl]-4-methyl-3,4-dihydro-2H-1,4-benzoxazine-8-carboxamide 2 fumarate. Melting point: 160°–161° C. (decomposed)

EXAMPLE 20

To a solution of 0.3 g of 6-chloro-2,2-diphenyl-4-methyl-3,4-dihydro-2H-1,4-benzoxazine-8-carboxylic acid in 10 ml of ethyl acetate was added 0.16 g of triethylamine. To the mixture was added dropwise 0.098 g of pivaloyl chloride with ice-cooling to −10° to −5° C., and stirred for 15 minutes at the temperature. To the reaction mixture was added 0.103 g of 3-aminoquinuclidine at −10° to −5° C., and the resulting mixture was stirred at room temperature for 1 hour. The reaction mixture was then washed with water, dried with anhydrous magnesium sulfate, and concentrated. To the residue was added ethanolic hydrochloric acid, and the precipitated crystals were collected by filtration and recrystallized from ethanol, thereby obtaining 6-chloro-2,2-diphenyl-4-methyl-N-(3-quinuclidinyl)-3,4-dihydro-2H-1,4-benzoxazine-8-carboxamide hydrochloride as colorless crystals. Melting point: 192°–194° C.

EXAMPLE 21

A solution of 2 g of 6-chloro-4-methyl-3,4-dihydro-2H-1,4-benzoxazine-8-carboxylic acid and 1.3 g of N-methylmorpholine in 10 ml of dimethylformamide and 20 ml of tetrahydrofuran was cooled to −15° to −20° C., and 1.2 g of isobutyl chloroformate was added thereto with stirring. Stirring was then continued for 20 minutes. To the liquid reaction mixture was added 1.4 g of (s)-(−)-2-aminomethyl-1-butylpyrrolidine, and the resulting mixture was stirred at room temperature for 4 hours. The reaction mixture was concentrated under reduced pressure to obtain residue. To the residue were then added an aqueous solution of potassium carbonate and ethyl acetate, and the resulting organic layer was separated, washed with water, and dried with magnesium sulfate. The solvent was distilled off under reduced pressure, and the residue was separated and purified by means of silica gel column chromatography, thereby obtaining (S)-(−)-N-[(1-butyl-2-pyrrolidinyl)methyl]-6-chloro-4-methyl-3,4-dihydro-2H-1,4-benzoxazine-8-carboxamide as oil. $[\alpha]_D = -63.7°$ C. (c=1, methanol).

EXAMPLE 22

A solution of 250 mg of 4-methyl-6-methylsulfonyl-3,4-dihydro-2H-1,4-benzoxazine-8-carboxylic acid and 186 mg of N-methylmorpholine in 4 ml of dimethylformamide and 4 ml of tetrahydrofuran was cooled to −15° to −20° C., and 126 mg of isobutyl chloroformate was added thereto with stirring. Stirring was then continued for 20 minutes. To the liquid reaction mixture was added 144 mg of 2-aminomethyl-1-butylpyrrolidine, and the resulting mixture was stirred at room temperature for 4 hours. To this mixture were then added an aqueous solution of potassium carbonate and ethyl acetate, and the resulting organic layer was separated, washed with water, and dried with magnesium sulfate. The solvent was distilled off under reduced pressure, and the residue was recrystallized from ethanol, thereby obtaining N-[(1-butyl-2-pyrrolidinyl)methyl]-4-methyl-6-methylsulfonyl-3,4-dihydro-2H-1,4-benzoxazine-8-carboxamide. Melting point: 110°–112° C.

EXAMPLE 23

To a solution of 1.8 g of 6-chloro-4-methyl-3,4-dihydro-2H-1,4-benzothiazine-8-carboxylic acid in 30 ml of ethyl acetate was added 1.05 g of triethylamine, and then added 0.891 g of pivaloyl chloride dropwise with stirring at −10° C. to −5° C. followed by stirring the mixture at the same temperature for 30 minutes. To the resultant mixture was added a solution of 1.12 g of 3-aminoquinuclidine in 15 ml of ethyl acetate at −10° to −5° C. and then stirred at room temperature for an hour. After the reaction solution was washed with water, dried over anhydrous sodium sulfate and concentrated, the crystalline residue thus obtained was recrystallized from ethyl acetate to give 6-chloro-4-methyl-N-(3-quinuclidinyl)-3,4-dihydro-2H-1,4-benzothiazine-8-carboxamide as yellow crystals. Melting point: 195°–196° C.

EXAMPLE 24

To a solution of 1.8 g of 6-chloro-4-methyl-3,4-dihydro-2H-1,4-benzothiazine-8-carboxylic acid in 30 ml of ethyl acetate was added 1.05 g of triethylamine, and then added 0.891 g of pivaloyl chloride dropwise with stirring at −10° C. to −5° C. followed by stirring the mixture at the same temperature for 30 minutes. To the resultant mixture was added 1.39 g of 2-aminomethyl-1-butylpyrrolidine at −10° C. to −5° C. and then stirred at room temperature for an hour. After the reaction solution was washed with water, dried over anhydrous sodium sulfate and concentrated, the residue thus obtained was crystallized from diisopropyl ether. The crystals were collected by filtration and recrystallized from diisopropyl ether to give N-[(1-butyl-2-pyrrolidinyl)methyl]-6-chloro-4-methyl-3,4-dihydro-2H-1,4-benzothiazine-8-carboxamide as colorless crystals. Melting point: 108°–109° C.

EXAMPLE 25

To a solution of 1.12 g of 6-chloro-2,2,4-trimethyl-3,4-dihydro-2H-1,4-benzoxazine-8-carboxylic acid in 30 ml of ethyl acetate was added 1.23 ml of triethylamine, and 0.53 g of pivalopyl chloride was added dropwise thereto at −10° to −5° C. under cooling. After stirring for 15 minutes at the same temperature, 0.62 g of endo-8-methyl-8-azabicyclo[3.2.1]oct-3-amine was added at −10° to −5° C. and the mixture was stirred at room temperature for an hour. The resultant mixture was washed with water, dried over magnesium sulfate and concentrated. To the residue was added ethanolic hydrochloric acid and the precipitated crystals were collected filtration and recrystallized from ethanol to give endo-6-chloro-2,2,4-trimethyl-N-(8-methyl-8-azabicyclo[3.2.1]oct-3-yl)-3,4-dihydro-2H-1,4-benzoxazine-8-carboxamide hydrochloride as white crystals, melting at 289°–293° C. with decomposition.

EXAMPLE 26

To a solution of 1.12 g of 6-chloro-2,2,4-trimethyl-3,4-dihydro-2H-1,4-benzoxazine-8-carboxylic acid in 30 ml of ethyl acetate was added 1.23 ml of triethylamine, and 0.53 g of pivaloyl chloride was added dropwise thereto at −10° to −5° C. under cooling. After stirring for 15 minutes at the same temperature, 0.68 g of endo-8-methyl-9-azabicyclo[3.2.1]nonan-3-amine was added at −10° to −5° C. and the mixture was stirred at room temperature for an hour. The resultant mixture was washed with water, dried over magnesium sulfate and concentrated. To the residue was added ethanolic hydrochloric acid and the precipitated crystals were collected filtration and recrystallized from ethanol to give endo-6-chloro-2,2,4-trimethyl-N-(9-methyl-9-azabicyclo[3.2.1]non-3-yl)-3,4-dihydro-2H-1,4-benzoxazine-8-carboxamide hydrochloride as white crystals, melting at 262° C. with decomposition.

EXAMPLE 27

To a solution of 1.5 g of 4-benzyl-6-chloro-2,2-dimethyl-3,4-dihydro-2H-1,4-benzoxazine-8-carboxylic acid in 30 ml of ethyl acetate was added 1.2 ml of triethylamine, and 0.55 g of pivaloyl chloride was added dropwise thereto at −10° to −5° C. under cooling. After stirring for 15 minutes at the same temperature, 0.57 g of 3-aminoquinuclidine was added at −10° to −5° C. and the mixture was stirred at room temperature for an hour. The resultant mixture was washed with water, dried over magnesium sulfate and concentrated. The precipitated crystals were collected by filtration and recrystallized from a mixed solvent of isopropyl ether and ethanol to give 4-benzyl-6-chloro-2,2-dimethyl-N-(3-quinuclidinyl)-3,4-dihydro-2H-1,4-benzoxazine-8-carboxamide as white crystals, melting at 174°–175° C.

EXAMPLE 28

To a solution of 1.0 g of 2,2,4-trimethyl-3,4-dihydro-2H-1,4-benzoxazine-8-carboxylic acid in 30 ml of ethyl acetate was added 1.2 ml of triethylamine, and 0.55 g of pivaloyl chloride was added dropwise thereto at −10° to −5° C. under cooling. After stirring for 15 minutes at the same temperature, 0.57 g of 3-aminoquinuclidine was added at −10° to −5° C. and the mixture was stirred at room temperature for an hour. The resultant mixture was washed with water, dried over magnesium sulfate and concentrated. The precipitated crystals were collected by filtration and recrystallized from a mixed solvent of isopropyl ether and ethanol to give 2,2,4-trimethyl-N-(3-quinuclidinyl)-3,4-dihydro-2H-1,4-benzoxazine-8-carboxamide as white crystals, melting at 114°–116° C.

EXAMPLE 29

To a solution of 1.5 g of 6-chloro-2,2-dimethyl-4-ethyl-3,4-dihydro-2H-1,4-benzoxazine-8-carboxylic acid in 30 ml of ethyl acetate was added 1.56 ml of triethylamine, and 0.67 g of pivaloyl chloride was added dropwise thereto at −10° to −5° C. under cooling. After stirring for 15 minutes at the same temperature, 0.70 g of 3-aminoquinuclidine was added at −10° to −5° C. and the mixture was stirred at room temperature for an hour. The resultant mixture was washed with water, dried over magnesium sulfate and concentrated. To the residue was added ethanolic hydrochloric acid and the precipitated crystals were collected by filtration and recrystallized from ethanol to give 6-chloro-2,2-dimethyl-4-ethyl-N-(3-quinuclidinyl)-3,4-dihydro-2H-1,4-benzoxazine-8-carboxamide hydrochloride as white crystals, melting at 273°–276° C.

According to methods similar to the above, the following compounds were prepared.

EXAMPLE 30

6-Fluoro-2,2,4-trimethyl-N-(3-quinuclidinyl)-3,4-dihydro-2H-1,4-benzoxazine-8-carboxamide hydrochloride, melting at 281°–285° C. with decomposition.

EXAMPLE 31

6-Bromo-2,2,4-trimethyl-N-(3-quinuclidinyl)3,4-dihydro-2H-1,4-benzoxazine-8-carboxamide hydrochloride, melting at 261°–264° C.

EXAMPLE 32

6-Chloro-2,2-dimethyl-4-propyl-N-(3-quinuclidinyl)-3,4-dihydro-2H-1,4-benzoxazine-8-carboxamide hydrochloride, melting at 244°–246° C.

EXAMPLE 33

6-Chloro-2,2-dimethyl-4-butyl-N-(3-quinuclidinyl)-3,4-dihydro-2H-1,4-benzoxazine-8-carboxamide hydrochloride, melting at 222°–223° C.

EXAMPLE 34

6-Chloro-2,2-dimethyl-4-(2-phenylethyl)-N-(3-quinuclidinyl)-3,4-dihydro-2H-1,4-benzoxazine-8-carboxamide hydrochloride, melting at 190°–192° C.

EXAMPLE 35

6-Chloro-2,2-dimethyl-N-(3-quinuclidinyl)-3,4-dihydro-2H-1,4-benzoxazine-8-carboxamide hydrochloride, melting at 273°–275° C. with decomposition

EXAMPLE 36

6-Chloro-2,4-dimethyl-N-(3-quinuclidinyl)-3,4-dihydro-2H-1,4-benzoxazine-8-carboxamide hydrochloride, melting at 283°–286° C. with decomposition

EXAMPLE 37

6-Chloro-4-methyl-2-phenyl-N-(3-quinuclidinyl)-3,4-dihydro-2H-1,4-benzoxazine-8-carboxamide hydrochloride, melting at 194°–196° C.

EXAMPLE 38

To a solution of 1.03 g of 6-chloro-2,2,4-trimethyl-3,4-dihydro-2H-1,4-benzoxazine-8-carboxylic acid in a mixed solvent of 5 ml of dimethylformamide and 10 ml of tetrahydrofuran was added 0.6 g N-methylmorpholine, and 0.55 g of isobutyl chloroformate was added dropwise thereto at −10° to −5° C. under ice-cooling. After stirring for 20 minutes at the same temperature, 0.63 g of (S)-(−)-2-aminomethyl-1-butylpyrrolidine was added at −10° to −5° C. and the mixture was stirred at room temperature for three hours. The resultant mixture was concentrated under reduced pressure, and to the residue were added an aqueous potassium carbonate solution and ethyl acetate. The organic layer was separated and washed with water and then dried over magnesium sulfate. The solvent was distilled off and the residue was recrystallized from isopropyl ether to give (S)-N-[(1-butyl-2-pyrrolidinyl)methyl]-6-chloro-2,2,4-trimethyl-3,4-dihydro-2H-1,4-benzoxazine-8-carboxamide as white crystals, melting at 110° to 112° C. $[\alpha]_D = -61.7°$ (c=1, methanol)

According to methods similar to the above, the following compounds were prepared.

EXAMPLE 39

(S)-N-[(1-Butyl-2-pyrrolidinyl)methyl]-4-methyl-6-methylthio-3,4-dihydro-2H-1,4-benzoxazine-8-carboxamide, $[\alpha]_D = -59.6°$ (c=1, methanol)

EXAMPLE 40

(R)-N-[(1-Butyl-2-pyrrolidinyl)methyl]-4-methyl-6-methylthio-3,4-dihydro-2H-1,4-benzoxazine-8-carboxamide, $[\alpha]_D = -61.5°$ (c=1, methanol)

EXAMPLE 41

(S)-N-[(1-Nonyl-2-pyrrolidinyl)methyl]-6-chloro-4-methyl-3,4-dihydro-2H-1,4-benzoxazine-8-carboxamide, $[\alpha]_D = -52.1°$ (c=1, methanol)

EXAMPLE 42

(S)-N-[{1-(2-Phenylethyl)-2-pyrrolidinyl}methyl]-4-methyl-6-nitro-3,4-dihydro-2H-1,4-benzoxazine-8-carboxamide, melting at 109°-111° C., $[\alpha]_D = -116.5°$ (c=0.8, methanol)

EXAMPLE 43

(R)-N-[{1-(2-Phenylethyl)-2-pyrrolidinyl}methyl]-4-methyl-6-nitro-3,4-dihydro-2H-1,4-benzoxazine-8-carboxamide, melting at 109°-111° C., $[\alpha]_D = -112.9°$ (c=1, methanol)

EXAMPLE 44

(R)-N-[(1-Benzyl-2-pyrrolidinyl)methyl]-4-methyl-6-methylthio-3,4-dihydro-2H-1,4-benzoxazine-8-carboxamide fumarate, melting at 120°°-122° C., $[\alpha]_D = -24.1°$ (c=1, methanol)

EXAMPLE 45

(S)-N-[{1-(2-Phenylethyl)-2-pyrrolidinyl}methyl]-6-chloro-4-methyl-1,4-dihydro-2H-1,4-benzoxazine-8-carboxamide, $[\alpha]_D = -94.9°$ (c=1, methanol)

EXAMPLE 46

(R)-N-[{1-(2-Phenylethyl)-2-pyrrolidinyl}methyl]-6-chloro-4-methyl-3,4-dihydro-2H-1,4-benzoxazine-8-carboxamide, $[\alpha]_D = +96.8°$ (c=1, methanol)

EXAMPLE 47

(S)-N-[(1-Octyl-2-pyrrolidinyl)methyl]-4-methyl-6-methylthio-3,4-dihydro-2H-1,4-benzoxazine-8-carboxamide, $[\alpha]_D = -52.0°$ (c=1, methanol)

EXAMPLE 48

(R)-N-[(1-Octyl-2-pyrrolidinyl)methyl]-4-methyl-6-methylthio-3,4-dihydro-2H-1,4-benzoxazine-8-carboxamide, $[\alpha]_D = +53.6°$ (c=1, methanol)

EXAMPLE 49

(S)-N-[(1Ethyl-2-pyrrolidinyl)methyl]-4-methyl-6-methylthio-3,4-dihydro-2H-1,4-benzoxazine-8-carboxamide, $[\alpha]_D = -41.5°$ (c=1, methanol)

EXAMPLE 50

(S)-N-[{1-(2-Phenylethyl)-2-pyrrolidiny}methyl]-6-chloro-2,2,4-trimethyl-3,4-dihydro-2H-1,4-benzoxazine-8-carboxamide, $[\alpha]_D = -75.5°$ (c=1, methanol)

EXAMPLE 51

N-[(1-Ethyl-2-pyrrolidinyl)methyl]-4-methyl-6-sulfamoyl-3,4-dihydro-2H-1,4-benzoxazine-8-carboxamide, melting at 175°-178° C.

EXAMPLE 52

(S)-N-[(1-Benzyl-2-pyrrolidinyl)methyl]-4-methyl-6-methylthio-3,4-dihydro-2H-1,4-benzoxazine-8-carboxamide fumarate, melting at 117°-118° C., $[\alpha]_D = -20.6°$ (c=1, methanol)

EXAMPLE 53

N-[(1-Ethyl-2-pyrrolidinyl)methyl]-4-methyl-3,4-dihydro-2H-1,4-benzoxazine-8-carboxamide, NMR spectra (CDCl$_3$; ppm): $\delta$=1.1(t, 3H), 1.4-2.0(4H), 2.0-2.5(2H), 2.5-3.5(9H), 3.5-3.9(m, 1H), 4.4(t, 2H), 6.4-7.0(2H), 7.4 (m, 1H), 8.1(brs, 1H)

EXAMPLE 54

N-[(1-Ethyl-2-pyrrolidinyl)methyl]-4-methyl-6-methylthio-3,4-dihydro-2H-1,4-benzoxazine-8-carboxamide, NMR spectra (CDCl$_3$; ppm) $\delta$=1.1(t, 3H), 1.4-2.0(4H), 2.0-2.4(2H), 2.5(s, 3H), 2.5-3.4(9H), 3.5-3.9(m, 1H), 4.3(t, 2H), 6.65(d, 1H), 7.4(d, 1H), 8.1(brs, 1H)

EXAMPLE 55

N-(1-Benzyl-4-piperidyl)-4-methyl-6-methylthio-3,4-dihydro-2H-1,4-benzoxazine-8-carboxamide oxalate, melting at 163°-165° C.

EXAMPLE 56

To a solution of 0.5 g of (S)-N-[{1-(2-phenylethyl)-2-pyrrolidinyl}-methyl]-4-methyl-6-nitro-3,4-dihydro-2H-1,4-benzoxazine-8-carboxamide in 50 ml of methanol was added 0.3 g of palladium carbon, and subjected to reduction under hydrogen atmosphere. After the catalyst was filtered off, the solvent was distilled off under reduced pressure. The residue was converted into the oxalate by treating with a solution of oxalic acid in methanol and recrystallized from methanol to give (S)-N-{1-(2-phenylethyl)-2-pyrrolidinyl}methyl]-6-amino-4-methyl-3,4-dihydro-2H-1,4-benzoxazine-8-carboxamide dioxalate, melting at 180°-182° C. with decomposition. $[\alpha]_D = -27.6°$ (c=0.5, methanol)

EXAMPLE 57

To a solution of 0.5 g of (R)-N-[{1-(2-phenylethyl)-2-pyrrolidinyl}methyl]-4-methyl-6-nitro-3,4-dihydro-2H-1,4-benzoxazine-8-carboxamide in 50 ml of methanol was added 0.3 g of palladium carbon, and subjected to reduction under hydrogen atmosphere. After the catalyst was filtered off, the solvent was distilled off under reduced pressure. The residue was converted into the oxalate by treating with a solution of oxalic acid in methanol and recrystallized from methanol to give (R)-N-[{1-(2-phenylethyl)-2-pyrrolidinyl}methyl]-6-amino-4-methyl-3,4-dihydro-2H-1,4-benzoxazine-8-carboxamide dioxalate, melting at 180°-181° C. with decomposition. $[\alpha]_D = +24.0°$ (c=0.5, methanol)

EXAMPLE 58

2,2-Benzyl-6-chloro-4-methyl-N-(3-quinuclidinyl)-3,4-dihydro-2H-1,4-benzoxazine-8-carboxamide

EXAMPLE 59 endo-2,2-Benzyl-6-chloro-4-methyl-N-(9-methyl-9-azabicyclo[3.2.1]non-3-yl)-3,4-dihydro-2H-1,4-benzoxazine-8-carboxamide

EXAMPLE 60

N-[(1-Buthyl-2-pyrrolidinyl)methyl]-2,2-benzyl-6-chloro-4-methyl-3,4-dihydro-2H-1,4-benzoxazine-8-carboxamide The present invention has been fully explained in the description and examples given above, but any variations and modifications thereof may be made without departing from the spirit and scope of the present invention.

What is claimed is:

1. A benzazine compound, a geometrical isomer of said benzazine compound, an optical isomer of said benzazine compound, and a pharmaceutically acceptable salt of said benzazine compound, said benzazine compound being represented by formula (I):

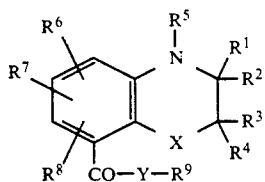

wherein both $R^1$ and $R^2$ represent hydrogen; $R^3$ and $R^4$ are the same or different and each represents hydrogen, an alkyl, phenyl or a phenylalkyl, provided that one of $R^3$ and $R^4$ represents hydrogen, an alkyl, phenyl or a phenylalkyl and the another represents an alkyl, phenyl or a phenylalkyl when $R^9$ represents a group of formula (a) or (c) as defined below; $R^5$ represents hydrogen, an alkyl, or a phenylalkyl; $R^6$ represents hydrogen, a halogen, an alkoxy, amino, nitro, $-S(O)_lR^{18}$ (wherein $R^{18}$ represents an alkyl, phenyl or a substituted phenyl and l is 0, 1 or 2), or

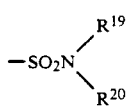

(wherein $R^{19}$ and $R^{20}$ are the same or different and each represents hydrogen or an alkyl); both $R^7$ and $R^8$ represent hydrogen; X represents oxygen or sulfur; Y represents $-NH-$; and $R^9$ represents a group of the formula:

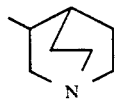

(a)

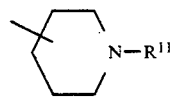

(b)

wherein $R^{11}$ represents an alkyl, a phenylalkyl, or a substituted phenylalkyl,

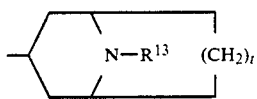

(c)

wherein t is 0 or 1 and $R^{13}$ represents an alkyl, a phenylalkyl, or a substituted phenylalkyl,

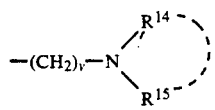

(d)

wherein $R^{14}$ and $R^{15}$ are bonded to each other to be a group which forms a heterocyclic ring in cooperation with the adjacent nitrogen atom, and v is an integer of 1 to 8, or

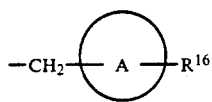

(f)

wherein ring A represents 2-pyrrolidine or 4-morpholine and $R^{16}$ represents hydrogen, an alkyl, an alkenyl, an alkynyl, a phenylalkyl, a substituted phenylalkyl, amino, a mono- or dialkyl-substituted amino, or an acylamino.

2. The compound of claim 1, wherein said compound is selected from the group consisting of 6-chloro-2,2,4-trimethyl-N-(3-quinuclidinyl)-3,4-dihydro-2H-1,4-benzoxazine-8-carboxamide, (R)-6-chloro-2,2,4-trimethyl-N-(3-quinuclidinyl)-3,4-dihydro-2H-1,4-benzoxazine-8-carboxamide, (S)-6-chloro-2,2,4-trimethyl-N-(3-quinuclidinyl)-3,4-dihydro-2H-1,4-benzoxazine-8-carboxamide, endo-6-chloro-2,2,4-trimethyl-N-(9-methyl-9-azabicyclo[3.3.1]non-3-yl)-3,4-dihydro-2H-1,4-benzoxazine-8-carboxamide, N-[(1-butyl-2pyrrolidinyl)methyl]-4-methyl-6-methylthio-3,4-dihydro-2H-1,4-benzoxazine-8-carboxamide, (S)-(−)-N-[(1-butyl-2pyrrolidinyl)methyl]-6-chloro-4-methyl-3,4-dihydro-2H-1,4-benzoxazine-8-carboxamide, 6-amino-N-[(1-butyl-2pyrrolidinyl)methyl]-4-methyl-3,4-dihydro-2H-1,4-benzoxazine- 8-carboxamide, 6-chloro-4-methyl-N-[(1-butyl-2-pyrrolidinyl)methyl]-3,4-dihydro-2H-1,4-benzoxazine-8-carboxamide, (R)-(+)-6-chloro-4-methyl-N-[(1-nonyl-2-pyrrolidinyl)methyl]-3,4-dihydro-2H-1,4-benzoxazine-8-carboxamide, 6-chloro-4-methyl-N-[(1-ethyl-2-pyrrolidinyl)methyl]-3,4-dihydro-2H-1,4-benzoxazine-8-carboxamide, (S)-N-[(1-butyl-2-pyrrolidinyl)methyl]-4-methyl-6-methylthio-3,4-dihydro-2H-1,4-benzoxazine-8-carboxamide, (R)-N-[(1-butyl-2-pyrrolidinyl)-methyl]-4-methyl-6-methylthio-3,4-dihydro-2H-1,4-benzoxazine-8-carboxamide, (S)-N-[{1-(2-phenylethyl)-2-pyrrolidinyl}methyl]-4-methyl-6-nitro-3,4-dihydro-2H-1,4-benzoxazine-8-carboxamide, (R)-N-[{1-(2-phenylethyl)-2-pyrrolidinyl}methyl]-4-methyl-6-nitro-3,4-dihydro-2H-1,4-benzoxazine-8-carboxamide, (S)-N-[{1-(2-phenylethyl)-2-pyrrolidinyl}methyl]-6-amino-4-methyl-3,4-dihydro-2H-1,4-benzoxazine-8-carboxamide and (R)-N-[(1-benzyl-2-pyrrolidinyl)methyl]-4-methyl-6-methylthio-3,4-dihydro-2H-1,4-benzoxazine-8-carboxamide and pharmaceutically acceptable salts thereof.

3. A benzazine compound, a geometrical isomer of said benzazine compound, an optical isomer of said benzazine compound, and a pharmaceutically acceptable salt of said benzazine compound, said benzazine compound being represented by formula (II):

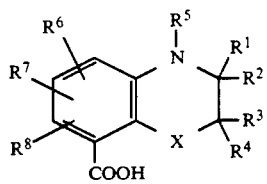

wherein each symbol has the same meaning as that defined in claim 1, or a reactive derivative thereof.

4. A pharmaceutical composition comprising the compound of claim 1 and a pharmaceutically acceptable carrier.

5. The compound of claim 1, wherein both $R^1$ and $R^2$ represent hydrogen; one of $R^3$ and $R^4$ represents hydrogen, an alkyl, phenyl or a phenylalkyl and the another represents an alkyl, phenyl or a phenylalkyl; $R^5$ represents hydrogen, an alkyl, or a phenylalkyl; $R^6$ represents hydrogen, a halogen, an alkoxy, amino, nitro, $-S(O)_lR^{18}$ (wherein $R^{18}$ represents an alkyl, phenyl or a substituted phenyl and l is 0, 1 or 2), or

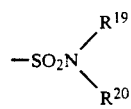

(wherein R$^{19}$ and R$^{20}$ are the same or different and each represents hydrogen or an alkyl); both R$^7$ and R$^8$ represent hydrogen; X represents oxygen or sulfur; Y represents —NH—; and R$^9$ represents a group of the formula:

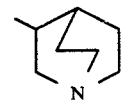

or

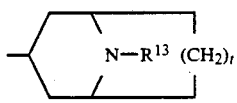

wherein t is 0 or 1 and R$^{13}$ represents an alkyl, a phenylalkyl, or a substituted phenylalkyl.

6. The compound of claim 5, wherein R$^6$ represents a halogen.

7. The compound of claim 5, wherein said compound is selected from the group consisting of 6-chloro-2,2,4-trimethyl-N-(3-quinuclidinyl)-3,4-dihydro-2H-1,4-benzoxazine-8-carboxamide, (R)-6-chloro-2,2,4-trimethyl-N-(3-quinucldinyl)-3,4-dihydro-2H-1,4-benzoxazine-8-carboxamide, (S)-6-chloro-2,2,4-trimethyl-N-(3-quinuclidinyl)-3,4-dihydro-2H-1,4-benzoxazine-8-carboxamide, endo- 6-chloro-2,2,4-trimethyl-N-(9-methyl-9-azabicyclo[3.3.1]non-3-yl)-3,4-dihydro-2H-1,4-benzoxazine-8-carboxamide, 6-chloro-2,4-dimethyl-N-(3-quinuclidinyl)-3,4-dihydro-2H-1,4-benzoxazine-8-carboxamide, endo-6-chloro-2,2,4-trimethyl-N-(8-methyl-8-azabicyclo[3.2.1]oct-3-yl)-3,4-dihydro-2H-1,4-benzoxazine-8-carboxamide and pharmaceutically acceptable salts thereof.

8. A pharmaceutical composition comprising the compound of claim 5 and a pharmaceutically acceptable carrier.

9. The compound of claim 1, wherein both R$^1$ and R$^2$ represent hydrogen; R$^3$ and R$^4$ are the same or different and each represents hydrogen, an alkyl, phenyl or a phenylalkyl; R$^5$ represents hydrogen, an alkyl, or a phenylalkyl; R$^6$ represents hydrogen, a halogen, an alkoxy, amino, nitro, —S(O)$_l$R$^{18}$ (wherein R$^{18}$ represents an alkyl, phenyl or a substituted-phenyl and l is 0, 1 or 2) or

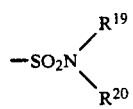

(wherein R$^{19}$ and R$^{20}$ are the same or different and each represents hydrogen or an alkyl); both R$^7$ and R$^8$ represents hydrogen; X represents oxygen or sulfur; Y represents —NH—; and R$^9$ represents a group of the formula:

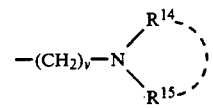

wherein R$^{11}$ represents an alkyl, a phenylalkyl, or a substituted phenylalkyl,

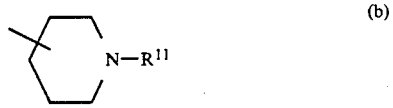

wherein R$^{14}$ and R$^{15}$ are bonded to each other to be a group which forms a heterocyclic ring in cooperation with the adjacent nitrogen atom, and v is an integer of 1 to 8, or

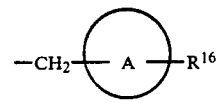

wherein ring A represents 2-pyrrolidine or 4-morpholine and R$^{16}$ represents hydrogen, an alkyl, an alkenyl, an alkynyl, a phenylalkyl, a substituted phenylalkyl, amino, a mono- or dialkyl-substituted amino, or an acylamino.

10. The compound of claim 9, wherein said compound is selected from the group consisting of N-[1-butyl-2-pyrrolidinyl)methyl]-4-methyl-6-methylthio-3,4-dihydro-2H-1,4-benzoxazine-8-carboxamide, (S)-(−)-N-[(-butyl-2-pyrrolidinyl)methyl]-6-chloro-4-methyl-3,4-dihydro-2H-1,4-benzoxazine-8-carboxamide, 6-amino-N-[(1-butyl-2-pyrrolidinyl)methyl]-4-methyl-3,4-dihydro-2H-1,4-benzoxazine-8-carboxamide, 6-chloro-4-methyl-N-[(1-butyl-2-pyrrolidinyl)methyl]-3,4-dihydro-2H-1,4-benzoxazine-8-carboxamide, (R)-(+)-6-chloro-4-methyl-N-[(1-nonyl-2-pyrrolidinyl)methyl]-3,4-dihydro-2H-1,4-benzoxazine-8-carboxamide, 6-chloro-4-methyl-N-[(1-ethyl-2-pyrrolidinyl)methyl]-3,4-dihydro-2H-1,4-benzoxazine-8-carboxamide, (S)-N-[(1-butyl-2-pyrrolidinyl)-methyl]-4-methyl-6-methylthio-3,4-dihydro-2H-1,4-benzoxazine-8-carboxamide, (R)-N-[(1-butyl-2-pyrrolidinyl)-methyl]-4-methyl-6-methylthio-3,4-dihydro-2H-1,4-benzoxazine-8-carboxamide, (S)-N-[{1-(2-phenylethyl)-2-pyrrolidinyl}-methyl]-4-methyl-6-nitro-3,4-dihydro-2H-1,4-benzoxazine-8-carboxamide, (R)-N-[{1-(2-phenylethyl)-2-pyrrolidinyl}-methyl]-4-methyl-6-nitro-3,4-dihydro-2H-1,4-benzoxazine-8-carboxamide, (S)-N-[{1-(2-phenylethyl)-2-pyrrolidinyl}-methyl]-6-amino-4-methyl-3,4-dihydro-2H-1,4-benzoxazine-8-carboxamide and (R)-N-[(1-benzyl-2-pyrrolidinyl)methyl]-4-methyl-6-methylthio-3,4-dihydro-2H-1,4-benzoxazine- 8-carboxamide and pharmaceutically acceptable salts thereof.

11. A pharmaceutical composition comprising the compound of claim 9, and a pharmaceutically acceptable carrier.

* * * * *